United States Patent [19]

Bertelson

[11] 4,200,752
[45] Apr. 29, 1980

[54] 4-DISUBSTITUTED AMINO, N-SUBSTITUTED NAPHTHALIMIDE DYESTUFFS

[76] Inventor: Robert C. Bertelson, 5312 Bliss Pl., Dayton, Ohio 45440

[21] Appl. No.: 878,395

[22] Filed: Feb. 16, 1978

[51] Int. Cl.² .......................................... C07D 221/14
[52] U.S. Cl. ................................ 546/100; 252/301.19
[58] Field of Search .................. 260/281 N, 281 NH; 546/100

[56] References Cited

U.S. PATENT DOCUMENTS

| 2,365,106 | 9/1945 | Scalera | 260/281 |
|---|---|---|---|
| 3,147,264 | 9/1964 | Klein | 260/281 |
| 3,362,958 | 1/1968 | Schellhammer | 260/281 NH |
| 3,386,920 | 6/1968 | Alburger | 252/301.2 |
| 3,425,950 | 2/1969 | Derbyshire | 252/301.2 |

FOREIGN PATENT DOCUMENTS

| 2415027 | 10/1975 | Fed. Rep. of Germany . |
| 753104 | 10/1933 | France . |
| 32-1809 | 3/1957 | Japan . |
| 39-7932 | 5/1964 | Japan . |

OTHER PUBLICATIONS

"Alternative Fluorescent Penetrant Formulations," Allinikov et al., Paper Summaries of the 1976 National Fall Conf. of the ASNT, pp. 181–183, 9/27/76.
Metals Handbook, 8th Ed., vol. 11, pp. 20–44, ASM Handbook Committee.
Sumitani et al., Chem. Abs. 77, 7306 (1971).
Loehe et al., Chem. Abs. 83, 61703s (1975).
Sato et al., Chem. Abs. 76, 15761s (1971).

*Primary Examiner*—Mark L. Berch
*Attorney, Agent, or Firm*—Dybvig & Dybvig

[57] ABSTRACT

The present disclosure is directed to novel quenchable, fluorescent dyestuffs which are substantially soluble in low surface tension, substantially non-polar oily solvents, e.g., refined kerosene, and are trisubstituted 4-aminonaphthalimides having the structure formula:

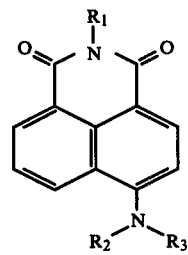

wherein
$R_1$ is a member selected from the group consisting of:
 (a) alkyl groups having from two to twelve carbon atoms,
 (b) substituted akyl groups having at least two carbon atoms,
 (c) phenylalkyl groups whose alkyl moiety has from one to four carbon atoms and
 (d) alicyclic rings having from five to six carbon atoms in the alicyclic ring;
$R_2$ and $R_3$ are members selected from the group consisting of:
 (a) alkyl groups having from one to twenty-two carbon atoms,
 (b) phenylalkyl groups whose alkyl moiety has from one to four carbon atoms,
 (c) alicyclic groups having up to twelve carbon atoms,
 (d) tetrahydrofuranylmethyl and
 (e) a single alkylene chain forming a single heterocyclic ring with the amino nitrogen;

with the provisos that the total number of carbon atoms in $R_1$, $R_2$ and $R_3$ is at least nine, and the total number of carbon atoms in $R_2$ and $R_3$ is at least four.

6 Claims, No Drawings

4-DISUBSTITUTED AMINO, N-SUBSTITUTED NAPHTHALIMIDE DYESTUFFS

BACKGROUND OF THE INVENTION

In the liquid penetrant non-destructive inspection of metal surfaces for cracks and flaws, liquid penetrant compositions are used to aid in visual examination to find the location of discontinuities in the surfaces being examined. One of the types of liquid penetrant materials used is the type containing fluorescent dyes, viz., dye substances which produce a readily visually observable color indication upon exposure of the fluorescent dye material to what is commonly called "black light" (ultraviolet light). Such materials greatly enhance the observability to the unaided eye when the surface is properly prepared and care is taken to insure that the liquid penetrants are applied, developed and/or selectively removed from the smooth continuous surfaces to insure contrast between the dye which penetrates into the surface discontinuities or flaws as compared with the remaining smooth or unflawed surfaces being examined.

It has been discovered that the dye substances which are the subject of this invention possess a unique combination of selective fluorescent properties in non-polar and highly polar liquid media, that renders them very useful in the field of liquid penetrant inspection. Typical dyestuffs of this invention when irradiated with ultraviolet light exhibit an intense luminescence when dissolved in a substantially non-polar liquid medium and exhibit a weak or no luminescence when dissolved in a substantially highly polar liquid medium. It is apparent that the substantially non-polar medium may be a mixture of miscible substances, and that the highly polar medium may also be a mixture of miscible substances. Further, the substantially highly polar medium containing one or more alcohols and glycols may include water.

Thus, for example, typical dyestuffs of this invention when irradiated with ultraviolet light will exhibit an intense luminescence when dissolved in a substantially non-polar oily medium: for example, refined kerosene or other aliphatic and/or alicyclic hydrocarbons; whereas said dyestuff will exhibit a weak or no luminescence when dissolved in a substantially highly polar liquid medium: for example, lower molecular weight alcohols such as methanol, ethanol, and isopropanol; glycols such as ethylene glycol, propylene glycol, and glycerol; and liquid organic acids such as acetic or propionic acids.

I have further found that when an intensely luminescing solution in a low surface tension non-polar solvent has added to it a high surface tension highly polar solvent the intensity of the luminescence decreases as the polar solvent is added until the intensity becomes very weak or negligible. That is, the luminescence of the original solution can be selectively "quenched." The term "quenchable" as used herein in reference to fluorescent dye penetrants refers to the ability of the subject dyestuffs to selectively alter their fluorescence intensity depending upon the polarity of the liquid medium in which they are dissolved, thus obtaining the disappearance of fluorescence in the background (smooth or non-flawed) areas to enhance the visual contrast between the dye which has penetrated the surface flaws or discontinuities and the dye which is contained on the non-flawed or smooth areas. The different surface tension characteristics of the non-polar and highly polar liquid media enable selective differentiation between the flawed and unflawed areas. The use of the dye substances of this invention enables the liquid penetrant inspection to be conducted with enhanced visual contrast, yet does not require removal of the quenching solution or liquid media, nor does it complicate the procedural aspects of the liquid penetrant inspection.

One novel use of such a selectively quenchable luminescent composition containing the dyestuffs of the present invention is in an improved process for the detection of flaws, wherein the luminescent composition is quenched selectively in the non-defective background areas of the object under inspection.

The dye substances of this invention are trisubstituted 4-aminonaphthalimides having one substituent ($R_1$) on the imide nitrogen, being a member selected from the group consisting of:

(a) alkyl groups having from two to twelve carbon atoms, (b) substituted alkyl groups having at least two carbon atoms, (c) phenylalkyl groups whose alkyl moiety has from one to four carbon atoms and (d) alicyclic rings having from five to six carbon atoms in the alicyclic ring;

The remaining two substituents ($R_2$ and $R_3$) are on the nitrogen atom of the 4-amino group, and are a member(s) selected from the group consisting of:

(a) alkyl groups having from one to twenty-two carbon atoms, (b) phenylalkyl groups whose alkyl moiety has from one to four carbon atoms, (c) alicyclic groups having up to twelve carbon atoms, (d) tetrahydrofuranylmethyl and (e) a single alkylene chain forming a single heterocyclic ring with the amino nitrogen;

with the foregoing two provisos.

It has been discovered that if $R_1$ has less than two carbon atoms, viz., $R_1$ is methyl, that such substances do not display suitable solubility properties to enable their use in liquid penetrant inspection procedures.

It has also been discovered that if $R_2$ and $R_3$ together have less than four carbon atoms, that such substances do not display suitable solubility properties to enable their use in liquid penetrant inspection procedures.

Suitable exemplary substituents for the $R_1$ position include, but are not necessarily limited to, the following: ethyl, n-propyl, n-butyl, 2-methoxyethyl, benzyl, 2-phenylethyl, cyclohexyl, and n-dodecyl. Suitable exemplary substituents at the $R_2$ and $R_3$ positions include, but are not necessarily limited to, the following: methyl, ethyl, n-propyl, n-butyl, benzyl, tetrahydrofurfuryl, isopropyl, cyclopentyl, cyclohexyl, cyclododecyl, and $C_{20-22}$ $H_{42-46}$, the corresponding secondary amine of which is "Kemamine S-190," a commercially available mixture of $C_{20}$ to $C_{22}$ secondary alkyl amines. In the case where $R_2$ and $R_3$ together with the nitrogen atom comprise a single heterocyclic ring, suitable exemplary ring substituents include, but are not necessarily limited to, piperidine and pyrrolidine.

Specific dye substances, within the purview of the aforementioned formula and having the desired combination of quenchable fluorescence and solubility are as follows: 4-methylbenzylamino-1,8-naphthalic acid-N-n-butylimide; 4-di-(n-propyl)amino-1,8-naphthalic acid-N-n-butylimide; 4-(1-piperidino)-1,8-naphthalic acid-N- n-butylimide; 4-(1-piperidino)-1,8-naphthalic acid-N-benzylimide; 4-methyltetrahydrofurfurylamino-1,8-naphthalic acid-N-n-butylimide; 4-di(n-butyl)amino-1,8-naphthalic acid-N-n-butylimide; 4-di(n-butyl)amino-1,8-naphthalic acid-N-cyclohexylimide; 4-di(n-propyl)amino-1,8-naphthalic acid-N-cyclohexylimide; 4-di(n-butyl)amino-1,8-naphthalic acid-N-benzylimide; and 4-di(n-propyl)amino-1,8-naphthalic acid-N-benzylimide. Other exemplary dyestuffs will be apparent from the TABLE following Example 5.

The liquid penetrant solutions, per se (absent quenching liquid media), can be prepared in accordance with known preparation procedures such as those indicated in the article entitled "Liquid Penetrant Inspection," pp. 20–44 of Vol. 11 of the American Society for Metals *Metals Handbook*, 8th Edition, published in 1976 and prepared by the American Society for Metals Handbook Committee.

The dyestuffs of this invention offer improved visual contrast between the discontinuous and continuous (flawed and unflawed) areas of the part being inspected when compared with known penetrant solutions.

THE PRIOR ART

U.S. Pat. No. 3,425,950 to Derbyshire, Jr., et al. discloses naphthalimides which are mono-substituted at the 4-amino group.

U.S. Pat. No. 3,386,920 to J. R. Alburger teaches dissolving fluorescent naphthalimide dyes in kerosene in liquid penetrant inspection procedures.

U.S. Pat. No. 3,147,264 to Klein discloses 4-mono (hydroxyalkylamino) naphthalic acid imide quaternary salts that are kerosene-soluble.

U.S. Pat. No. 2,385,106 to Scalera, et al. also discloses naphthalimides which are mono-substituted at the 4-amino position. Di-substituted 4-amino naphthalimides such as used by Derbyshire, Jr., et al. and discovered by Scalera, et al. are substantially ineffective when compared to the dyestuffs of this invention because I have found that the fluorescence of such compounds, when in a substantially non-polar solvent, cannot be quenched by the addition of a substantially highly polar medium, and therefore when they are used in a liquid penetrant solution they do not offer as great a visual contrast between the discontinuous and continuous areas of the part being inspected.

German Offenlegungsschrift No. 2415027 (inspection date Oct. 16, 1975) of H. Scheurmann, et al. discloses substituted naphthalimides which differ from the subject dye substances of this invention in that the substituent on the imide nitrogen must be either hydroxy or alkoxy.

Chemical Abstracts, 52, 9484a (1958) concerns Japanese Patent No. 32-1809 of March 20, 1957, entitled "Compositions for Fluorescent Penetrant Inspection," which discloses the known compound 4-dodecylamino-N-butyl,1,8-naphthalimide in a fluorescent penetrant composition. This is a di-substituted naphthalimide dyestuff wherein $R_3$ is hydrogen. It is not quenchable.

A disclosure of the compound 4-dimethylamino-N-methyl-1,8-naphthalimide can be found at Chemical Abstracts, 61, 16211h (1964) referring to Japanese Patent No. 39-7932 of May 19, 1964. This compound is not suitable for practical use as a quenchable dye substance in liquid penetrant inspection because its solubility in approved, substantially non-polar median, e.g., kerosene, is very low. The resulting penetrant composition does not exhibit sufficiently intense fluorescence to greatly enhance the visual observability of a flaw.

PREPARATION OF DYESTUFFS OF THIS INVENTION

The dyestuffs of this invention can be prepared by a variety of procedures.

According to one method, basically two steps are involved: first, a 4-bromo or 4-chloro-1,8-naphthalic anhydride is allowed to react with a primary amine of the formula $R_1NH_2$ and the reaction product is purified in accordance with known procedures for materials of this type. The intermediate so obtained is then caused to react with an amine of the formula $R_2NHR_3$ (where $R_2$ and $R_3$ are as defined herein above) in a second step which can be carried out in comparatively polar solvents, e.g., dimethyl formamide, dimethyl sulfoxide, and ethylene glycol.

According to another method, the second step can be carried out in the same inert diluent without the necessity of first isolating the intermediate. Scalera, et al., U.S. Pat. No. 2,385,106 refers to the use of the same water-immiscible inert diluent in what may be termed a "straight-through" two-step procedure not involving the necessity of first isolating the intermediate.

In accordance with a third procedure, the novel dyestuffs of this invention can be prepared in a straight-through two-step process utilizing a comparatively polar, water-imiscible solvent in the absence of any cupriferous catalyst or additional acid-binding substance. For this two-step procedure the preferred polar solvent is dimethyl sulfoxide. Of the three procedures indicated above, the two-step dimethyl sulfoxide procedure is preferred because it is the most convenient. It is preferred over the first method because it avoids the additional time and labor involved in separating and purifying the intermediate, and it is preferred over the straight-through process taught by Scalera, et al. because the product may be precipitated from the reaction mixture merely by addition of water, thereby avoiding the energy-costly step of removing the diluent by means of distillation or steam distillation.

The invention will be illustrated in greater detail in conjunction with the following examples in which the proportions, percentages, and parts are by weight unless otherwise indicated.

EXAMPLE 1

($R_1$ is n-butyl and $R_2$ and $R_3$ are n-propyl)

A 12-liter reaction vessel fitted with a stirrer, a thermometer, a dropping funnel, and a heating mantle was charged with 1330 grams of 4-bromo-1,8-naphthalic anhydride and four liters of dimethyl sulfoxide. The mixture was brought to 100° C. and while being stirred was treated during one and one-half hours with a solution of 349 grams of n-butylamine in 800 milliliters of dimethyl sulfoxide, the temperature being kept at 100° C. throughout. After the end of the addition the mixture was held at 100° C. for an additional hour. Next was added 971 grams of di(n-propyl)amine during a fifteen-minute period, the stirring being maintained throughout. The reaction mixture was then gradually brought to a temperature of 150° C. during a three-hour period, and held at that temperature for an additional six hours. The solution was cooled to near ambient temperature and diluted with four liters of toluene. The diluted solution was treated with eight liters of water and allowed to separate into two layers. The upper toluene layer was washed with water, dried, and evaporated to leave N-butyl-4-di(n-propyl)aminonaphthalimide as a dark orange, waxy solid. The amount of material obtained approached the theoretical yield of 1690 grams.

EXAMPLE 2

(R₁ is n-butyl, R₂ is methyl and R₃ is benzyl)

In a manner similar to that described in Example 1, 5.58 parts of the bromonaphthalic anhydride were caused to react successively with 1.46 parts of n-butylamine and 2.42 parts of benzylmethylamine to afford 5.45 parts (73% of the theoretical yield) of 4-methylbenzylamino-1,8-naphthalic acid-N-n-butylimide as yellow orange crystals exhibiting a melting point of 106°–108° C. In this case the product can be precipitated as a solid directly from the reaction mixture by addition of water, and the preliminary dilution with toluene can be omitted.

EXAMPLE 3

(R₁ is n-butyl, R₂ is methyl or tetrahydrofurfuryl and R₃ is tetrahydrofurfuryl or methyl)

Proceeding as in Example 2 but replacing the benzylmethylamine with 2.30 parts of tetrahydrofurfurylmethylamine gave 4-methyltetrahydrofurfurylamino-1,8-naphthalic acid-N-n-butylimide as a very viscous yellow oil.

EXAMPLE 4

(R₁ is benzyl and R₂ and R₃ are piperidino)

In a manner similar to that described in Example 1, 5.58 parts of the bromonaphthalic anhydride were allowed to react successively with 2.14 parts of benzylamine and 3.40 parts of piperidine. Dilution with water alone at the end of the reaction precipitated 6.70 parts, or 90%, of yellow-orange crystals of N-benzyl-4(1-piperidino)naphthalimide having a melting point of 149°–151° C.

EXAMPLE 5

(R₁ is n-butyl and R₂ and R₃ are piperidino)

Proceeding as in Example 4, but replacing the benzylamine with 1.46 parts of n-butylamine gives N-butyl-4-(1-piperidino)naphthalimide as yellow crystals exhibiting a melting point of 127°–130° C.

Still further examples of the naphthalimides of this invention can be prepared in a manner similar to that described in Example 1, by reaction of 4-bromonaphthalic anhydride first with an amine chosen from Column A in the Table, and then with a secondary amine chosen from Column B in the Table.

TABLE

Reactants for Preparing Trisubstituted 4-Aminonaphthalimide Dyestuffs

| Column A | Column B |
|---|---|
| 1. $C_2H_5NH_2$ | 1. $C_2H_5NHC_2H_5$ |
| 2. $n-C_3H_7NH_2$ | 2. $n-C_3H_7NHC_3H_7$ |
| 3. $n-C_4H_9NH_2$ | 3. $n-C_4H_9NHC_4H_9$ |
| 4. $N-C_{12}H_{25}NH_2$ | 4. $(CH_3)_2CHNHCH_3$ (isopropyl methylamine) |
| 5. $n-C_{18}H_{37}NH_2$ | 5. $C_6H_5CH_2NHCH_3$ (benzyl methylamine) |
| 6. ⬡—$NH_2$ (cyclohexylamine) | 6. $C_6H_5CH_2NHCH_2C_6H_5$ (dibenzyl amine) |
| 7. $CH_3OCH_2CH_2NH_2$ | 7. ⬡—$NHCH_3$ (methyl cyclohexylamine) |
| 8. $C_6H_5CH_2NH_2$ | 8. ⬡NH (piperidine) |
| 9. $C_6H_5CH_2CH_2NH_2$ | 9. ⬠NH (pyrrolidine) |
| | 10. (tetrahydrofurfuryl methyl amine) |

I claim:

1. Quenchable fluorescent dyestuffs which are substantially soluble in low surface tension substantially non-polar oily solvents and have the formula:

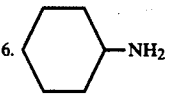

wherein
R₁ is a member selected from the group consisting of:
 (a) alkyl groups having from two to twelve carbon atoms,
 (b) alkyl groups having from two to three carbon atoms and substituted with a methoxy or an ethoxy group,
 (c) phenylalkyl groups whose alkyl moiety has from one to four carbon atoms and
 (d) monocyclic alicyclic rings having from five to six carbon atoms in the alicyclic ring;
R₂ and R₃ are members selected from the group consisting of:
 (a) alkyl groups having from one to twenty-two carbon atoms,
 (b) phenylalkyl groups whose alkyl moiety has from one to four carbon atoms,
 (c) monocyclic alicyclic groups having up to twelve carbon atoms,
 (d) tetrahydrofuranylmethyl and
 (e) a single alkylene chain forming a single heterocyclic ring with the amino nitrogen, said ring containing five or six members;
with the provisos that the total number of carbon atoms in R₁, R₂ and R₃ is at least nine, and the total number of carbon atoms in R₂ and R₃ is at least four.

2. N-n-butyl-4-di(n-propyl)aminonaphthalimide.
3. N-n-butyl-4-methylbenzylaminonaphthalimide.
4. N-n-butyl-4-methyltetrahydrofurfurylaminonaphthalimide.
5. N-benzyl-4(1-piperidino)naphthalimide.
6. N-butyl-4-(1-piperidino)naphthalimide.

* * * * *

UNITED STATES PATENT AND TRADEMARK OFFICE
CERTIFICATE OF CORRECTION

PATENT NO. : 4,200,752
DATED : April 29, 1980
INVENTOR(S) : Robert C. Bertelson

It is certified that error appears in the above-identified patent and that said Letters Patent are hereby corrected as shown below:

In the Abstract, line 5, "structure" should be ---structural---.

In the Abstract, line 10, "akyl" should be ---alkyl---.

Col. 3, line 67, "median" should be ---media---.

Col. 4, line 29, "water-imiscible" should be ---water-miscible---.

Col. 5, line 48, "point point" should be ---point---.

In the Table, Col. A, in item 4, "N—" should be ---n- ---.

Signed and Sealed this

Second Day of September 1980

[SEAL]

Attest:

SIDNEY A. DIAMOND

Attesting Officer

Commissioner of Patents and Trademarks